(12) United States Patent
Huth et al.

(10) Patent No.: US 12,710,001 B2
(45) Date of Patent: Aug. 18, 2026

(54) REAL-TIME SYSTEM AND METHOD FOR DETERMINING REMAINING USEFUL OIL LIFE IN VEHICLES

(71) Applicant: Cummins Inc., Columbus, IN (US)

(72) Inventors: Anthony J. Huth, Cincinnati, OH (US); Ryan E. Denton, Franklin, IN (US); David A. Fields, Columbus, IN (US); John Y. Howland, Columbus, IN (US); Michael T. Hughes, Columbus, IN (US); Corey W. Trobaugh, Columbus, IN (US)

(73) Assignee: Cummins Inc., Columbus, IN (US)

( * ) Notice: Subject to any disclaimer, the term of this patent is extended or adjusted under 35 U.S.C. 154(b) by 43 days.

(21) Appl. No.: 18/714,088

(22) PCT Filed: Nov. 28, 2022

(86) PCT No.: PCT/US2022/051082
§ 371 (c)(1),
(2) Date: May 28, 2024

(87) PCT Pub. No.: WO2023/097078
PCT Pub. Date: Jun. 1, 2023

(65) Prior Publication Data

US 2025/0035018 A1 Jan. 30, 2025

Related U.S. Application Data

(60) Provisional application No. 63/283,685, filed on Nov. 29, 2021.

(51) Int. Cl.
*G07C 5/04* (2006.01)
*F01M 11/10* (2006.01)
(Continued)

(52) U.S. Cl.
CPC ............ *F01M 11/10* (2013.01); *G01N 33/30* (2013.01); *G07C 5/006* (2013.01); *F01M 2011/14* (2013.01); *G07C 5/04* (2013.01)

(58) Field of Classification Search
CPC ........... F01M 11/10; G01N 33/30; G07C 5/04
See application file for complete search history.

(56) References Cited

U.S. PATENT DOCUMENTS 9,280,856 B2 3/2016 Chen et al.
9,714,931 B2 7/2017 Prabhu et al.
(Continued)

FOREIGN PATENT DOCUMENTS

| | | | | |
|---|---|---|---|---|
| CN | 112440903 A | | 3/2021 | |
| EP | 3 677 755 A1 | | 7/2020 | |
| WO | WO-2018136583 A1 | * | 7/2018 | ............ F01M 11/12 |

OTHER PUBLICATIONS

PCT Search Report and Written Opinion issued Mar. 28, 23 for PCT Application No. PCT/US2022/051082.
(Continued)

*Primary Examiner* — Adnan M Mirza
(74) *Attorney, Agent, or Firm* — Foley & Lardner LLP

(57) ABSTRACT

A computing system is disposed remote from a vehicle and communicably coupled to the vehicle over a network. The computing system includes: a communication interface structured to communicably couple to the network; one or more processors; and a memory storing instructions that, when executed by the one or more processors, cause the one or more processors to: receive, via the communication interface and from a vehicle, vehicle operational data and vehicle metadata; determine a lubricant oxidation rate based on a statistical model; determine a lubricant drain interval based on the lubricant oxidation rate relative to a predefined lubricant oxidation limit; and, provide the lubricant drain
(Continued)

interval to an output device. The lubricant may be a lubricant for the vehicle, such as oil.

18 Claims, 6 Drawing Sheets

(51) Int. Cl.
*G01N 33/30* (2006.01)
*G07C 5/00* (2006.01)

(56) References Cited

U.S. PATENT DOCUMENTS

| | | | | |
|---|---|---|---|---|
| 10,473,009 | B2 | 11/2019 | Sworski et al. | |
| 2008/0027661 | A1 | 1/2008 | Aikawa | |
| 2013/0197830 | A1 | 8/2013 | Dvorak et al. | |
| 2015/0192560 | A1 | 7/2015 | Basu et al. | |
| 2018/0144388 | A1 | 5/2018 | Mattern et al. | |
| 2018/0202333 | A1 | 7/2018 | Sworski et al. | |
| 2018/0231518 | A1 | 8/2018 | Vaidya et al. | |
| 2019/0016337 | A1 | 1/2019 | Yu | |
| 2019/0156600 | A1 | 5/2019 | Potyrailo et al. | |
| 2020/0234515 | A1* | 7/2020 | Gronsbell | G07C 5/12 |

OTHER PUBLICATIONS

Extended Search Report issued for European Patent Application No. 22899437.2 issued Sep. 29, 2025.

* cited by examiner

REAL-TIME SYSTEM AND METHOD FOR DETERMINING REMAINING USEFUL OIL LIFE IN VEHICLES

CROSS-REFERENCE TO RELATED APPLICATIONS

This application is a National Stage Entry of International Application No. PCT/US2022/051082, filed Nov. 28, 2022, which claims the benefit of and priority to U.S. Application No. 63/283,685, filed Nov. 29, 2021, the contents of which are incorporated herein by reference in their entireties.

TECHNICAL FIELD

The present disclosure relates to systems and methods for determining a remaining useful lubricant, such as oil, life in vehicles in real-time or near real-time.

BACKGROUND

Oil is primarily used as lubrication in vehicles (e.g., in internal combustion engines to facilitate movement and reduce overheating of a crankshaft, piston, camshaft, etc.). Lubricant oil may become oxidized over time. The oxidation degrades the performance of the lubricant oil thereby putting the internal combustion engine at risk for damage. Vehicle and/or engine manufacturers may publish recommendations for replacing lubricant oil based on a time period or a number of miles traveled. However, some vehicles may require more frequent or less frequent lubricant oil changes. In this regard, the published recommendations may be generalized and not custom to a particular vehicle and operation of that vehicle. Therefore, strict adherence to published recommendations for when an oil change is required may lead to more frequent oil changes than needed or, worse yet, too infrequent oil changes which may lead to unwanted damage occurring within the vehicle. Further, in fleet situations, the individual vehicles can have extremely different duty cycles such that having one or even a few oil drain intervals for the fleet is ineffective (e.g., leading to over/under estimated oil drain intervals that practically results in too frequent or too in-frequent service events).

SUMMARY

One embodiment relates to a computing system. In one embodiment, the computing system is a provider computing system (e.g., a fleet manager computing system, a vehicle engine or other system/component computing system). The computing system is disposed remote from a vehicle and communicably coupled to the vehicle over a network. The computing system includes: a communication interface structured to communicably couple to the network; one or more processors; a memory storing instructions that, when executed by the one or more processors, cause the one or more processors to: receive, via the communication interface and from a vehicle, vehicle operational data and vehicle metadata; determine a lubricant oxidation rate based on a statistical model; determine a lubricant drain interval based on the lubricant oxidation rate; and, provide the lubricant drain interval to an output device. In one embodiment, the lubricant is oil.

In some embodiments, the lubricant oxidation rate is based on less than four operational data values. In some embodiments, the lubricant oxidation rate is based on a fuel economy, an idle time of an engine of the vehicle, and a power take-off time of the vehicle.

The instructions, when executed by the one or more processors, may further cause the one or more processors to compare the lubricant drain interval to a predefined lubricant drain interval and in response to the comparison, cause an indicator on the vehicle to illuminate. In some embodiments, in response to the comparison, the one or more processors are further configured to generate and provide a map to the vehicle with a direction to a service location, where the map is displayed by the vehicle. In some embodiments, in response to the comparison, the one or more processors are further configured to trigger one or more fault codes for the vehicle. In some embodiments and in response to the comparison, the one or more processors are further configured to derate an engine of the vehicle by transmitting an instruction over the network via the communication interface.

The instructions, when executed by the one or more processors, may further cause the one or more processors to parse the vehicle metadata from the vehicle operational data and associate the vehicle metadata with a record associated with the vehicle. In one embodiment, the one or more processors are further configured to remove the vehicle metadata before determining the lubricant oxidation rate.

Another embodiment relates to a method of determining a lubricant drain interval. The method includes: receiving, by a computing system, vehicle operational data and vehicle metadata from a vehicle; determining, by the computing system, a lubricant oxidation rate based on a statistical model based at least in part on the vehicle operational data; determining, by the computing system, a lubricant drain interval based on the lubricant oxidation rate; and, providing, by the computing system, the lubricant drain interval to an output device. In some embodiments of the method, determining the lubricant oxidization rate is based on less than four operational data values. In some embodiments, the method also includes comparing the lubricant drain interval to a predefined lubricant drain interval; and responsive to determining that the lubricant drain interval exceeds the predefined lubricant drain interval, causing an indicator on the vehicle to illuminate. The method may also include responsive to determining that the lubricant drain interval exceeds the predefined lubricant drain interval, generating a map comprising a direction to a service location, and providing the map to the vehicle where the map is displayable by the vehicle. The method may also include responsive to determining that the lubricant drain interval exceeds the predefined lubricant drain interval, triggering, by the computing system, one or more fault codes for the vehicle. The method may also include responsive to determining that the lubricant drain interval exceeds the predefined lubricant drain interval, derating, by the computing system, an engine of the vehicle by transmitting an instruction over the network via the communication interface.

In some embodiments, the method also includes modifying the lubricant drain interval by a predetermined factor such that a modified lubricant drain interval is greater than the lubricant drain interval.

Yet another embodiment relates to a system. The system includes a controller coupled to an engine and at least one sensor of a vehicle. The controller includes one or more processors and at least one memory coupled to the one or more processors. The at least one memory stores instructions therein that, when executed by the one or more processors, cause the one or more processors to: receive vehicle operational data from the at least one sensor; generate an operational data packet comprising at least one of the vehicle operational data, trend data, or metadata; determine an oxidation rate based on the operational data packet and a statistical model; determine a lubricant drain interval based on the oxidation; generate a lubricant drain interval reporting data packet; and provide the lubricant drain interval reporting data packet to an output device. The instructions, when executed by the one or more processors, may further cause the one or more processors to transmit the operational data packet to the output device prior to determining the oxidation rate. The oxidation rate may be further based on one or more engine parameters. The one or more engine parameters may include at least one of a fuel economy, an idle time, or a power take off time. In some embodiments, the lubricant oxidation rate is based on less than four operational data values.

In some embodiments, the instructions, when executed by the one or more processors, further cause the one or more processors to: receive at least one of (i) one or more data sets or (ii) one or more regression equations from the output device, and determine the lubricant drain interval based on the at least one of (i) the one or more data sets or (ii) the one or more regression equations.

This summary is illustrative only and is not intended to be in any way limiting. Numerous specific details are provided to impart a thorough understanding of embodiments of the subject matter of the present disclosure. The described features of the subject matter of the present disclosure may be combined in any suitable manner in one or more embodiments and/or implementations. In this regard, one or more features of an aspect of the invention may be combined with one or more features of a different aspect of the invention. Moreover, additional features may be recognized in certain embodiments and/or implementations that may not be present in all embodiments or implementations.

Figure 1:
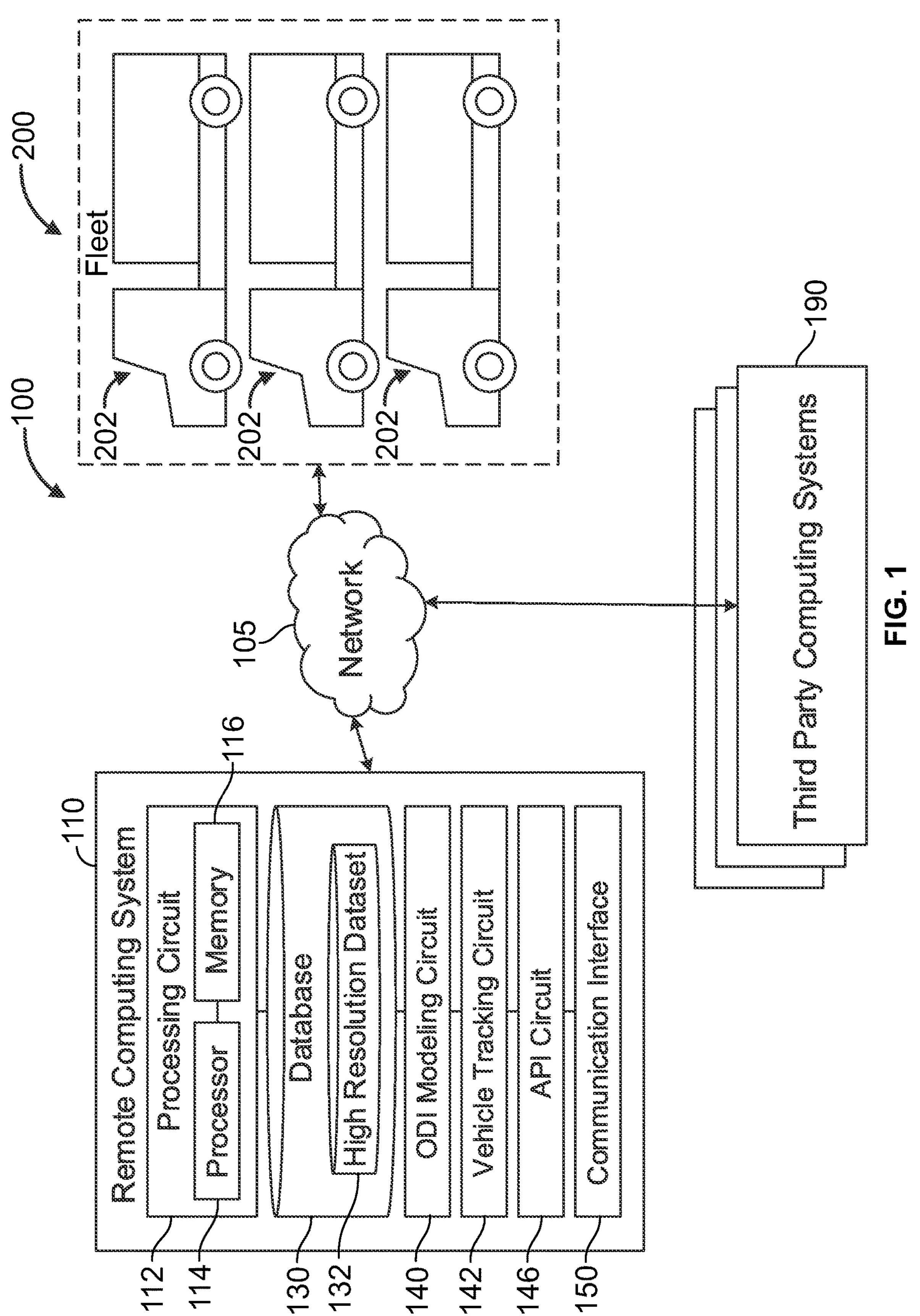
FIG. 1 is a block diagram of a computing system for determining a remaining useful oil life in vehicles in real-time or near real-time, according to an example embodiment.

These and other features, together with the organization and manner of operation thereof, will become apparent from the following detailed description when taken in conjunction with the accompanying drawings.

DETAILED DESCRIPTION

Following below are more detailed descriptions of various concepts related to, and implementations of methods, apparatuses, and systems for oil drain interval modeling, application of the model, and in turn real-time remaining useful oil life determinations and notifications regarding the remaining useful oil life determinations. The various concepts introduced herein may be implemented in any number of ways, as the concepts described are not limited to any particular manner of implementation. Examples of specific implementations and applications are provided primarily for illustrative purposes.

Referring to the Figures generally, the various embodiments disclosed herein relate to systems, apparatuses, and methods for modeling remaining useful oil life in vehicles in real-time (e.g., every second, every minute, every hour, etc.) or periodically (e.g., every trip made by a vehicle, every day, every week, etc.). A controller (e.g., an engine control module (ECM) or engine control unit (ECU)) for a vehicle includes at least one processor and at least one memory storing instructions that, when executed by the processor, cause the controller to perform various operations. The operations include detecting one or more operational parameters of the vehicle such as an engine fuel economy, a power-take off time for an engine of the vehicle, an idle time of the engine, and the like. The one or more operational parameters may be transmitted to a remote (e.g., off-vehicle) computing system such as a cloud computing system. An oil drain interval is calculated or determined based on the operational parameters and known vehicle parameters such as an engine type, engine oil type used, etc. The ODI is provided to a third party computing system (e.g., a customer computing system) via an application programming interface (API). Alternatively or additionally, the ODI is provided by the remote computing system back to the controller of the vehicle.

As described herein, the ODI is calculated or determined based on one or more datasets. The datasets include high resolution data relating to operational parameters of engines and engine systems. The datasets are used to generate a statistical model of an oil degradation rate (e.g., an oxidation rate). In one embodiment, a statistical regression is performed on the datasets to determine an equation for generating a computer-generated prediction of an oxidation rate based on certain operational data of a vehicle. The ODI is calculated by comparing the oxidation rate to an oxidation limit determined based on one or more characteristics of the engine or vehicle, which may be provided to the remote computing system via metadata. The one or more characteristics of the engine or vehicle may include, but is not limited to, a characteristic of an engine, such as an engine type, an engine size, etc. In some embodiments, the ODI is calculated by a remote computing system such as a cloud computing system. Accordingly, the remote computing system includes relevant hardware and/or software including the one or more datasets. In some embodiments, the ODI is calculated by an on-board computing device such as a specialized controller in a vehicle. In some embodiments, the on-board computing device includes the one or more datasets. In other embodiments, the on-board computing device is structured to access the one or more datasets and/or regression equations from the remote computing system.

The systems and methods described herein provide a technical solution to a technical problem of determining an oil drain interval (ODI—also referred to herein as "lubricant drain interval") to reduce risk of engine damage and/or reduce vehicle ownership costs for one or more vehicles in a fleet. For example, in any of the above embodiments, the ODI is reported to a vehicle owner or operator (e.g., a business, fleet operator, a user, etc.). The ODI advantageously allows the vehicle owner to drain and change lubricant oil based on specific parameters of the particular vehicle (e.g., instead of a manufacturer recommended or average oil drain interval). The vehicle-specific ODI advantageously mitigates against engine damage by recommending oil changes sooner than a manufacturer recommendation in vehicles that oxidize or degrade lubricant oil more quickly (e.g., vehicles that have a higher than normal duty cycle or operate in extreme conditions). Further, the vehicle-specific ODI advantageously reduces vehicle ownership costs by reducing the frequency of lubricant oil changes for vehicles that oxidize or degrade lubricant oil less quickly. These and other features and benefits are described more fully herein below.

While the term "oil" is used predominately herein, this description is not meant to be limiting as the systems, methods, and apparatuses are applicable with other lubricants including, but not limited to, grease, penetrating lubricants, etc. In this regard, the terms lubricant and oil are used interchangeably herein. The instant disclosure is primarily directed to lubricant oil for an internal combustion engine and associated systems/components. Accordingly, the oil type may be highly configurable (e.g., regular, synthetic, long-life, etc. and be of a variety of SAE grades). Notwithstanding and as alluded to above, the features, benefits, and aspects of the disclosure may also be applicable to other lubricants such that the description herein pertaining to engine lubricant is not meant to be limiting. As used herein, the term ODI refers to the period of time between oil changes. An ODI is often specified by the manufacturer of an engine or other components as a function of distance traveled by the vehicle. As described herein, a real-time vehicle-specific ODI is determined based on, for example, one or more engine operational parameters, such as a distance traveled, engine run time, etc., that advantageously promotes better care for the vehicle and engine.

Referring now to FIG. 1, a block diagram of a system 100 for calculating or determining a remaining useful oil life in vehicles in real-time or near real-time is shown, according to an example embodiment. As shown in FIG. 1, the system 100 includes a network 105, a remote computing system 110, a fleet 200 of vehicles 202, and one or more third party computing systems 190. Each of the components of the system 100 are in communication with each other and are coupled by the network 105. Specifically, the remote computing system 110, the third party computing systems 190, and computing systems and/or vehicle controllers of the vehicles 202 of the fleet 200 are communicatively coupled to the network 105 such that the network 105 permits the direct or indirect exchange of data, values, instructions, messages, and the like (represented by the double-headed arrows in FIG. 1). In some arrangements, the network 105 is configured to communicatively couple to additional computing system(s). In operation, the network 105 facilitates communication of data between the remote computing system 110 and other computing systems associated with the service provider or with a customer of the service provider (e.g., a vehicle or fleet owner) such as a user device (e.g., a mobile device, smartphone, desktop computer, laptop computer, tablet, or any other suitable computing system). The network 105 may include one or more of a cellular network, the Internet, Wi-Fi, Wi-Max, a proprietary provider network, a proprietary service provider network, and/or any other kind of wireless and/or wired network.

The remote computing system 110 is a remote computing system such as a remote server, a cloud computing system, and the like. Accordingly as used herein, "remote computing system" and "cloud computing system" are interchangeably used to refer to a computing or data processing system that has terminals distant from the central processing unit (e.g., processing circuit 112) from which users and/or other computing systems (e.g., the third party computing systems 190 and/or computing systems of the vehicles 202) communicate with the central processing unit. In some embodiments, the remote computing system 110 is part of a larger computing system such as a multi-purpose server, or other multi-purpose computing system. In other embodiments, the remote computing system 110 is implemented on a third party computing device operated by a third party service provider (e.g., AWS, Azure, GCP, and/or other third party computing services). The remote computing system 110 is operated by the service provider associated with the system 100. Accordingly, in some embodiments, the remote computing system 110 is a service and/or system/component provider computing system and in turn controlled by, managed by, or otherwise associated with service and/or system/component provider (e.g., an engine manufacturer, a vehicle manufacturer, an exhaust aftertreatment system manufacturer, etc.). In the example shown, the remote computing system 110 is operated and managed by an engine manufacturer (which may also manufacture and commercialize other goods and services). Accordingly, an employee or other operator associated with the service and/or system/component provider may operate the remote computing system 110.

As shown in FIG. 1, the remote computing system 110 includes a processing circuit 112, a database 130, one or more specialized processing circuits shown as an ODI modeling circuit 140 and a vehicle tracking circuit 142, and a communications interface 150. The processing circuit 112 is coupled to the specialized processing circuits, the database 130 and/or the communications interface 150. The processing circuit 112 includes a processor 114 and a memory 116. The memory 116 is one or more devices (e.g., RAM, ROM, Flash memory, hard disk storage) for storing data and/or computer code for completing and/or facilitating the various processes described herein. The memory 116 is or includes non-transient volatile memory, non-volatile memory, and non-transitory computer storage media. The memory 116 includes database components, object code components, script components, or any other type of information structure for supporting the various activities and information structures described herein. The memory 116 is communicatively coupled to the processor 114 and includes computer code or instructions for executing one or more processes described herein. The processor 114 is implemented as one or more application specific integrated circuits (ASICs), field programmable gate arrays (FPGAs), a group of processing components, or other suitable electronic processing components. As such, the remote computing system 110 is configured to run a variety of application programs and store associated data in a database and/or the memory 116.

The communications interface 150 is structured to receive communications from and provide communications to other computing devices, users, and the like associated with the remote computing system 110. The communications interface 150 is structured to exchange data, communications, instructions, and the like with an input/output device of the components of the system 100. In some arrangements, the communications interface 150 includes communication circuitry for facilitating the exchange of data, values, messages, etc. between the communications interface 150 and the components of the remote computing system 110. In some arrangements, the communications interface 150 includes machine-readable media for facilitating the exchange of information between the communications interface 150 and the components of the remote computing system 110. In some arrangements, the communications interface 150 includes any combination of hardware components, communication circuitry, and machine-readable media.

In some embodiments, the communications interface 150 includes a network interface. The network interface is used to establish connections with other computing devices by way of the network 105. The network interface includes program logic that facilitates connection of the remote computing system 110 to the network 105. In some arrangements, the network interface includes any combination of a wireless network transceiver (e.g., a cellular modem, a Bluetooth transceiver, a Wi-Fi transceiver) and/or a wired network transceiver (e.g., an Ethernet transceiver). For example, the communications interface 150 includes an Ethernet device such as an Ethernet card and machine-readable media such as an Ethernet driver configured to facilitate connections with the network 105. In some arrangements, the network interface includes the hardware and machine-readable media sufficient to support communication over multiple channels of data communication. Further, in some arrangements, the network interface includes cryptography capabilities to establish a secure or relatively secure communication session in which data communicated over the session is encrypted.

In an example embodiment, the communications interface 150 is structured to receive information from the vehicles 202 and provide the information to the components of the remote computing system 110. The communications interface 150 is also structured to transmit data from the components of the remote computing system 110 to the third party computing systems 190.

The memory 116 may store a database 130, according to some arrangements (alternatively, the database 130 may be separate from the memory 116). The database 130 retrievably stores data associated with the remote computing system 110 and/or any other component of the system 100. That is, the data includes information associated with each of the components of the system 100. For example, the data includes information about one or more vehicles 202 of the fleet 200. The information about the fleet 200 includes information received from one or more vehicles 202 and/or metadata including information about the one or more vehicles 202. For example, the information includes location information such as a vehicle location and/or a vehicle distance traveled. The information also includes fuel usage information such as an engine fuel usage rate, a total fuel usage over a predetermined time period or distance, an engine fuel usage while idle, an engine fuel usage for a trip, and/or a total engine power take off fuel used. The information also includes engine run, idle, and/or power take off (PTO) time information such as a total hours of operation, a total hours of idling, and/or a total hours of PTO in a predetermined time period. The metadata may include an engine serial number, a vehicle identification number (VIN), a calibration identification and/or verification number, a software identification, a make of the vehicle, a model of the vehicle, a unit number of a power unit of the vehicle, and/or a vehicle maintenance history. Any of the data described above may include additional metadata such as a timestamp of when the data was gathered and/or when the data was transmitted or received by the remote computing system 110. The predetermined time periods described above may include a trip time, a work week, an actual ODI time period, a predicted ODI time period, a predetermined vehicle lifespan, and the like. The data also includes information associated with the third party computing systems 190 such as customer information including a number of vehicles owned, fleet identifiers, one or more vehicle identifiers, data reporting preferences, vehicle maintenance history, and/or any other information associated with the third party computing systems 190. The fleet data and/or the third party computing systems data are retrievable, viewable, and/or editable by the remote computing system 110 (e.g., by a user input).

As shown in FIG. 1, the database 130 stores the data, described above, as a high resolution dataset 132. As used herein, a "high resolution dataset" is a dataset that includes a large amount of data provided by a plurality of data sources over a predetermined time period (e.g., an actual ODI, a predicted ODI, one year, two years, etc.). Accordingly the high resolution dataset 132 includes vehicle data, vehicle metadata, and third party data received from a plurality of vehicles 202 and third party computing systems 190 over a predetermine time period. The high resolution dataset 132 includes location information, fuel usage information, engine operational parameters, metadata, and/or any additional data related to the operation of the vehicles 202. The high resolution dataset 132 also includes a maintenance history including time stamps of maintenance service, historical oil oxidation (e.g., in abs/cm or abs/cm/mile), and/or other maintenance data related to the vehicles 202. The high resolution dataset 132 also includes data from vehicles outside of the fleet 200. That is, the high resolution dataset 132 includes data from vehicles from multiple fleets.

The database 130 may be configured to store one or more applications and/or executables to facilitate tracking data (e.g., vehicle data, fleet data, and/or third party data), managing real-time incoming data, generating or updating statistical models, or any other operation described herein. In some arrangements, the applications and/or executables are incorporated with an existing application in use by the remote computing system 110. In some arrangements, the applications and/or executables are separate software applications implemented on the remote computing system 110. The applications and/or executables may be downloaded by the remote computing system 110 prior to its usage, hard coded into the memory 116 of the processing circuit 112, or be a network-based or web-based interface application such that the remote computing system 110 provides a web browser to access the application, which may be executed remotely from the remote computing system 110 (e.g., by a user device). Accordingly, the remote computing system 110 includes software and/or hardware capable of implementing a network-based or web-based application. For example, in some instances, the applications and/or executables include software such as HTML, XML, WML, SGML, PHP (Hypertext Preprocessor), CGI, and like languages.

In the latter instance, a user (e.g., a provider employee, a customer, etc.) may log onto or access the web-based interface before usage of the applications and/or executables. In this regard, the applications and/or executables are supported by a separate computing system including one or more servers, processors, network interface, and so on, that transmit applications for use to the remote computing system 110.

In one embodiment, and as shown in FIG. 1, the remote computing system 110 includes an ODI modeling circuit 140 that includes any combination of hardware and software for making computer-generated predictions or estimates based on one or more statistical models. The ODI modeling circuit 140 is structured to determine, predict, and/or estimate via a statistical model an ODI based on the high resolution dataset 132 (e.g., vehicle operational data, vehicle metadata, etc.).

For example, the remote computing system 110 is structured to receive data from the one or more vehicles 202, in real-time or periodically and via the communications interface 150 and/or the vehicle tracking circuit 142. The received data is stored in the database 130 (e.g., with the high resolution dataset 132). The ODI modeling circuit 140 generates one or more statistical models based on the high resolution dataset 132. The statistical models include, for example, a relationship between an oxidation rate and one or more vehicle parameters.

The ODI modeling circuit 140 is also structured to generate a regression model equation based on the one or more statistical models. The ODI modeling circuit 140 determines, based on generating the regression models, a best fit equation. In one embodiment, the best fit equation is selected based on an r-squared value associated with the regression models. For example, the ODI modeling circuit 140 may generate a multi-variable regression equation that relates an oxidation rate to one or more vehicle operational parameters. In one example embodiment, the vehicle operational parameters include a fuel efficiency, and an idle and PTO time. In other embodiments, the vehicle operational parameters include more than three parameters, less than three parameters, and/or different vehicle operational parameters related to the vehicles 202. In some embodiments, ODI modeling circuit 140 is further structured to receive real-time information from the vehicles 202 (e.g., via the communications interface 150 and/or the vehicle tracking circuit 142) and update the statistical models and/or regression equation based on the received information.

In an example embodiment, the regression equation may include one or more constants determined by a statistical analysis of the statistical models. Accordingly, the equation outputs an oxidation rate in absorbance per centimeter per unit miles and includes constants di, and d with inputs of vehicle operational parameters $x_i$. As alluded to above and in an example embodiment, the vehicle operational parameters (e.g., duty cycle parameters) may include an average engine load total (%), a drive average power total (horsepower), an average engine speed total (RPM), a fuel economy (e.g., in MPG), a drive average fuel economy (e.g., in MPG), a fuel consumption rate (gallon/hour), an idle fuel consumption rate (gallon/hour), a power take off fuel consumption rate (gallon/hour), a sum of idle and power take off fuel consumption rates (gallon/hour), an idle time (%), a PTO time (%), a sum of idle and PTO time (%), a full load operation time (%), a fuel used for idle (%), a fuel used for PTO (%), a sum of fuel used for idle and PTO (%), and/or a vehicle speed (e.g., in MPH). In one embodiment and as mentioned above, the oxidation rate is based on the parameters of fuel economy, idle time, and PTO time, where the idle and PTO time are relative values of the idle and PTO being active relative to a total amount of operation of the vehicle. With reference to Equation (1) below, these parameters would represent $x_0$ (fuel economy) and $x_1$ (sum of idle and PTO time (%)) with no other parameters included. As mentioned above, in other embodiments, different, more, or less parameters may be used. Further, the parameters may be combined in different manners, such as idle fuel consumption rate and power take off may represent $x_0$ or some other parameter in Equation (1) below. Thus, the example above is only meant to be illustrative and not limiting. Based on the foregoing, an example equation, shown as Equation (1), is as follows:

$$\text{Oxidation Rate} = da_0 + a_1(x_0) + a_2(x_0)^2 + a_3(x_1) + a_4(x_1)^2 + a_5(x_2) + a_6(x_2)^2 + \ldots + a_j(x_i) + a_{j+1}(x_i)^2 \quad (1)$$

The ODI modeling circuit 140 is further structured to generate a computer-generated prediction of an oil drain interval based on the oxidation rate of a particular vehicle 202 and a metadata associated with the vehicle, such as an oxidation limit. For example, the ODI, in miles, is calculated by comparing the oxidation rate, in absorbance per centimeter per mile, to an oxidation limit, in absorbance per centimeter, as shown in Equation (2) below.

$$\text{Oil Drain Interval} = \frac{\text{Oxidation Limit}}{\text{Oxidation Rate}} \quad (2)$$

Accordingly, the ODI modeling circuit 140 generates a computer-generated prediction of an oil drain interval based on the oxidation rate determined based on received operational parameters. In some embodiments, the ODI modeling circuit 140 is structured to derive additional predictions or estimates based on the calculated ODI. For example, the ODI modeling circuit 140 is structured to determine a number of miles until an oil change is required or may be required, a number of miles (or other unit of distance) until an oil change is or may be required, a number of hours until an oil change is or may be required, a number of engine hours until an oil change is or may be required, a percentage of oil life remaining, a percentage of oil life used, a number of days until an oil change is or may be required, and a date of when an oil change is or may be required. The predicted ODI, and any derivation thereof, is provided to the API circuit 146.

In some embodiments, the remote computing system 110 includes any combination of hardware and software including specialized processing circuits, applications, executables, and the like for controlling, managing, or facilitating the operation of the other computing systems of the system 100 including the third party computing systems 190 and computing systems of the vehicles 202 of the fleet 200. For example, the remote computing system 110 includes a vehicle tracking circuit 148 and associated software for tracking the vehicles 202 of the fleet 200. For example, the vehicle tracking circuit 148 is structured to receive (e.g., via the communication interfaces 150) information about the vehicles 202 of the fleet 200 such as the information described above with respect to the high resolution dataset 132 and/or any other information associated with the vehicle.

The API circuit 146 is structured to host and manage an API that is accessible by computing systems (e.g., the third party computing systems 190) associated with the network 105. For example, the API is accessible to computing systems via the communications interface 150. The API circuit 146 is structured receive a predicted ODI from the ODI modeling circuit 140. The API circuit 146 is further structured to provide the predicted ODI to one or more computing systems (e.g., the third party computing systems 190) that access the API.

The third party computing systems 190 include one or more computing systems associated with one or more third parties (e.g., parties that are not the service provider). For example, the third party computing systems 190 may include a computing system associated with a direct customer, a third party customer (e.g., a customer of the direct customer), and/or any other party of interest. For example and in one embodiment, the third party computing system 190 is associated with a fleet operator (e.g., a trucking company that has at least one truck). In some embodiments, a third party computing system registers with the remote computing system 110 to be included in the third party computing systems 190. After registration, the remote computing system 110 may provide the determined ODI for vehicles of the fleet specific to the third party computing system 190 associated with that specific vehicle.

The third party computing systems 190 include processing circuitry that may be similar to the processing circuit 112 and a communications interface similar to the communications interface 150 such that the third party computing systems 190 are operable to communicate with the remote computing system 110 and/or the fleet 200 via the network 105. For example, the third party computing systems 190 may access the API hosted by the API circuit 146 via a communications interface.

As shown in FIG. 1, the fleet 200 includes one or more vehicles 202. In some embodiments, the fleet 200 includes more or fewer vehicles (e.g., at least one vehicle). The fleet 200 is associated with at least one of the service provider, a direct customer of the service provider, a third party customer, a location (e.g., a city, a state, a region, a country, etc.), a vehicle type (e.g., engine type, chassis type, workload type, etc.), and/or any other parameter associated with the vehicle. For example, the fleet 200 may be associated with a first customer, and may include one or more vehicles 202. In the example shown, the fleet 200 is associated with a third-party that operates, controls, uses, and/or is associated with a third party computing system 190.

Figure 2:
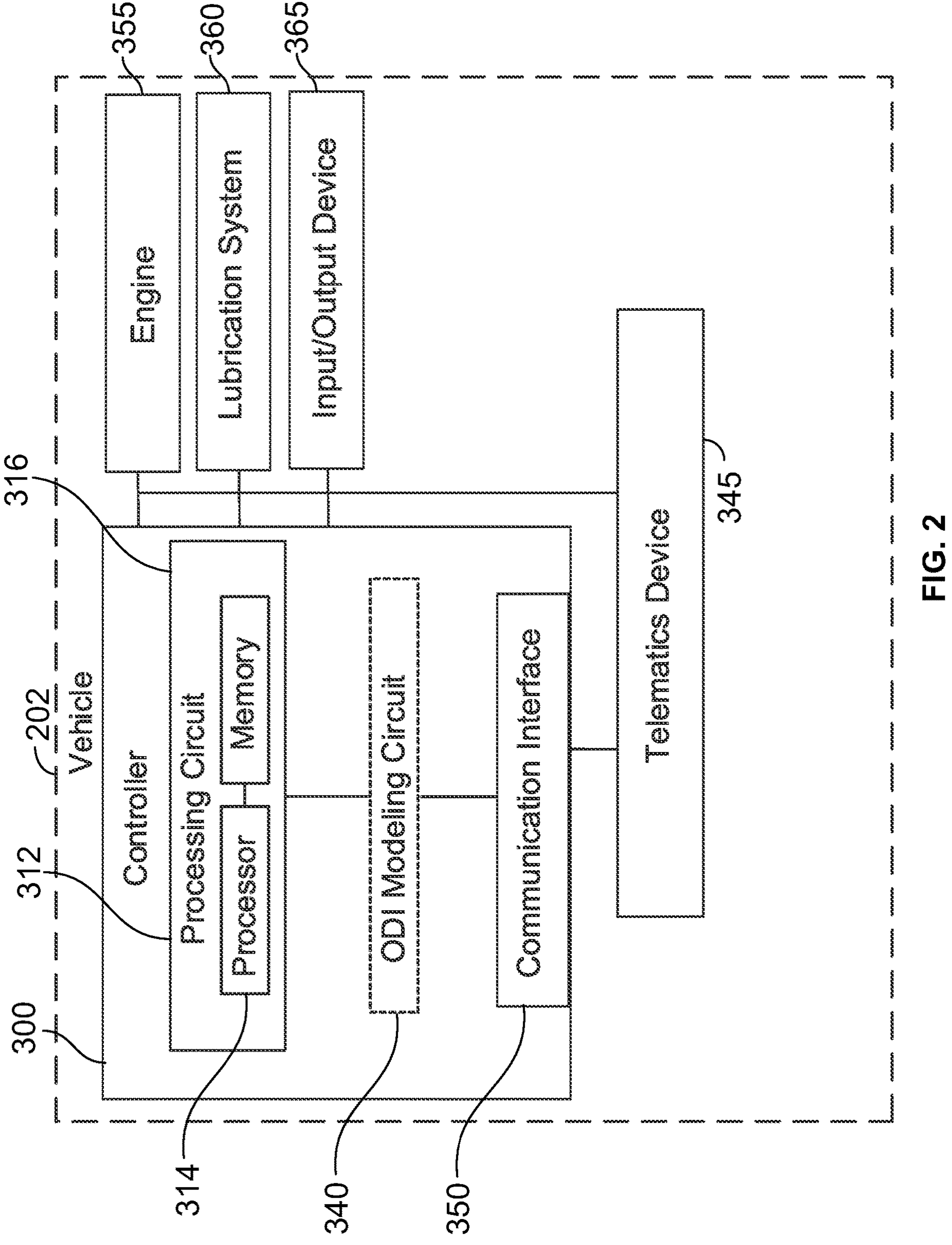
FIG. 2 is a block diagram of a vehicle of the system of FIG. 1, according to an example embodiment.

FIG. 2 is a block diagram of a vehicle 202 of the system of FIG. 1, according to an example embodiment. The vehicle any type of passenger or commercial automobile, such as a commercial on-road vehicle including but not limited to, a line haul truck (e.g., a semi-truck, a school bus, a garbage truck, etc.); a non-commercial on-road vehicle, such as a car, truck, sport utility vehicle, cross-over vehicle, van, minivan, automobile; an off-road vehicle, such as tractor, airplane, boat, forklift, front end loader, etc.; a stationary vehicle (e.g., a generator, an air compressor); and/or any other type of machine or vehicle that is suitable for the systems described herein.

The vehicle 202 is shown to include an engine 355 coupled to a lubrication system 360. The engine 355 may be any type of internal combustion engine, such as a gasoline, natural gas, and/or diesel engine, and/or any other suitable engine. In some embodiments, the engine 355 may be embodied in a hybrid engine system (e.g., a combination of the internal combustion engine and an electric motor). In the example shown, the engine 355 is a diesel-powered compression-ignition engine. The engine 355 includes one or more cylinders and associated pistons whereby the one or more cylinders may be arranged in a variety of ways (e.g., v-arrangement, inline, etc.). Air from the atmosphere is combined with fuel, and combusted, to produce power for the vehicle. Combustion of the fuel and air in the compression chambers of the engine 355 produces exhaust gas that is operatively vented to an exhaust pipe and to, in some embodiments, an exhaust aftertreatment system.

The lubrication system 360 circulates lubricant, such as oil, to various parts of the vehicle 202, such as the engine 355 in order to reduce friction and wear on moving parts, to provide cooling, and to generally maintain desired operation of the vehicle 202 components. In this regard, the lubricant may be circulated to a variety of components for providing lubrication, such as a crankshaft of the engine 355, cylinder walls of the engine 355, camshafts coupled to the engine 355, gears, a turbocharger coupled to the engine, bearings disposed throughout the vehicle 202, and so on. The lubrication system 360 may include a number of conduits, pipes, tubes, etc., a lubricant sump, a pump, and a filtration system (among potentially other components and systems). The conduits facilitate the circulation of lubricant through the lubrication system 360. The lubricant sump is a storage reservoir where lubricant is stored. The controller 300 controls the pump (e.g., turns it on/off, varies it displacement power, etc.) to draw the lubricant from the lubricant sump and routes the lubricant through the filtration system, to the engine 355, and back to the lubricant sump via the conduits. The lubricant sump is a storage reservoir (e.g., a tank) that stores lubricant not being circulated through the lubrication system 360. The filtration system includes a filter element. The filter element includes filter media (e.g., fibrous filter media, paper filter media, Nano-fiber filter media, and/or the like). The filter media is structured to capture and remove contaminants (e.g., water, dust, debris, etc.) from the lubricant upstream of the internal combustion engine in a lubricant flow direction. The filter element requires periodic replacement as the filter media captures the contaminants.

While not shown, in some embodiments, the vehicle 202 may include an exhaust aftertreatment system configured to treat exhaust gas emitted from the engine 355 to reduce the emissions of harmful gases to the environment (e.g., NOx, greenhouse gases, carbon monoxide, particulate matter, and so on). Thus, the exhaust after treatment system may include selective catalytic reduction (SCR) catalyst, a diesel oxidation catalyst (DOC), a diesel particulate filter (DPF), a diesel exhaust fluid (DEF) doser with a supply of diesel exhaust fluid, a plurality of sensors for monitoring the aftertreatment system (e.g., a nitrogen oxide (NOx) sensor, temperature sensors, flow rate sensors, etc.), and/or still other components. The arrangement of these components may be in a variety of ways depending on the application.

The vehicle 202 includes a sensor array that includes a plurality of sensors. The sensors are coupled to the controller 300, such that the controller 300 can monitor, receive, and/or acquire data indicative of operation of the vehicle 202 (which may be referred to as operational data associated with the vehicle herein). In this regard, the sensor array may include one or more physical (real) or virtual sensors. For example, the sensor array may include temperature sensors. The temperature sensors acquire data indicative of or, if virtual, determine an approximate temperature of various components or systems, such as the exhaust gas at or approximately at their disposed location. The sensor array may also include NOx sensors (or sensors for other emissions) that acquire data indicative of or, if virtual, determine an approximate amount of NOx (or other exhaust gas constituent emissions) in the exhaust gas stream at or approximately at their disposed locations (e.g., immediately downstream of the engine 355, immediately downstream of the aftertreatment system, etc.). A speed sensor is configured to provide a speed signal to the controller 300 indicative of a vehicle speed. In some embodiments, there may be a sensor that provides a speed of the vehicle (e.g., miles-per-hour) while in other embodiments the speed of the vehicle may be determined by other sensed or determined operating parameters of the vehicle (e.g., engine speed in revolutions-per-minute may be correlated to vehicle speed using one or more formulas, a look-up table(s), etc.). The sensor array may also include a fuel tank level sensor that determines a level of fuel in the vehicle 202, such that a fuel economy may be determined based on the speed of the vehicle relative to the fuel consumed by the engine 355 (i.e., to determine a distance-per-unit of fuel consumed, such as miles-per-gallon or kilometers-per-liter, etc.). Additional sensors may be used alone or in combination to determine a fuel economy for the vehicle 202 include, but are not limited to, an oxygen sensor, an engine speed sensor, a mass air flow (MAF) sensor, and a manifold absolute pressure sensor (MAP). Based on the foregoing, the controller 300 may determine a fuel economy for the vehicle 202 which may be provided to the operator via the I/O device 365 and, in some embodiments, transmitted to the remote computing system 110 for use by, for example, the ODI modeling circuit 140.

The sensor array may include a flow rate sensor that is structured to acquire data or information indicative of flow rate of a gas or liquid through the vehicle (e.g., exhaust gas through an aftertreatment system or fuel flow rate through an engine, exhaust gas recirculation flow at a particular location, a charge flow rate at a particular location, an oil flow rate at various positions, a hydraulic flow rate at a particular location, etc.). The flow rate sensor(s) may be coupled to an aftertreatment system of the vehicle 202 and/or elsewhere in the vehicle 202.

The sensor array may further include any other sensors. Such sensors may be used to determine a duty cycle for the vehicle 202, and particularly, the engine 355. A duty cycle refers to a repeatable set of data, values, or information indicative of how the specific vehicle is being utilized for a particular application. In particular, a "duty cycle" refers to a repeatable set of vehicle operations for a particular event or for a predefined time period. For example, a "duty cycle" may refer values indicative of a vehicle speed for a given time period. In another example, a "duty cycle" may refer to values indicative of an aerodynamic load on the vehicle for a given time period. In yet another example, a "duty cycle" may refer to values indicative of a vehicle speed and an elevation of a vehicle for a given time period. In this regard and compared to a vehicle drive cycle, which is typically limited to time versus speed information, the term "duty cycle" as used herein is meant to be broadly interpreted and inclusive of vehicle drive cycles among other quantifiable metrics. Beneficially and based on the foregoing, the "duty cycle" may be representative of how a vehicle may operate in a particular setting, circumstance, or environment (e.g., a seventy-file mile stretch of a relatively flat freeway environment). In this regard, the vehicle duty cycle may vary greatly based on the vehicle (e.g., a two-door sedan vehicle versus a concrete mixer truck versus a refuse truck versus a semi-tractor trailer vehicle). Duty cycle parameters may include therefore, but are not limited to, average engine load for a predefined time period (which may be determined by a MAP sensor or other sensors), a fuel consumption rate per time (e.g., gallons-per-hour as determined by a fuel consumption sensor), a fuel economy per unit of time, a value indicative of an amount time that the vehicle is in an idle (i.e., not moving such as when the vehicle is in a park transmission setting), a value indicative of an amount time that the power take off (PTO) is active, etc. The PTO indicates that the engine 355 is powering some specific piece of equipment or performing a certain predefined function (e.g., a crane of the vehicle, operating front-end loader, powering a fork lift, powering a concrete mixer drum, etc.). The PTO being engaged or active may be determined by the controller 300 when the piece of equipment or function is receiving power (e.g., a timer may be set/triggered when power to that piece of equipment identified). Based on the foregoing, the controller 300 may track a total operation time based on total engine hours (total time engine is/was on) which may then be demarcated by vehicle drive time (time engine was on and vehicle was moving as evidenced by a vehicle speed above a threshold amount, such as zero miles-per-hour), PTO time (time specific equipment is being powered by engine or a specific function is being powered by the engine), idle time (time engine is on but the vehicle is not moving and the PTO specific function/specific equipment is not being powered), and other demarcation possibilities.

It should be understood that other different/additional sensors may also be included with the vehicle 202, such as an accelerator pedal position (APP) sensor, a pressure sensor, an engine torque sensor, a battery sensor, etc. Those of ordinary skill in the art will appreciate and recognize the high configurability of the sensors and their associated positions in the vehicle 202. The controller 300 is structured to provide the operational data to the remote computing system 110 via the communications interface 350 or, in some embodiments, via the telematics device 345. In some embodiments, the controller 300 may provide certain data/information to the third party computing system 190.

The vehicle 202 may also include an operator input/output (I/O) device 365. The operator I/O device 365 may be communicably coupled to the controller 300, such that information may be exchanged between the controller 300 and the I/O device 365, where the information may relate to one or more components of the vehicle 202, information received from the remote computing system 110, and/or one or more determinations of the controller 300. The operator I/O device 365 enables an operator of the system 100 to communicate with the controller 300 and one or more components of the vehicle 202 of FIG. 1. For example, the operator input/output device 365 may include, but is not limited to, an interactive display, a touchscreen device, one or more buttons and switches, voice command receivers, etc. In this way, the operator input/output device 365 may provide one or more indications or notifications to an operator, such as a malfunction indicator lamp (MIL), etc. Additionally, the vehicle 202 may include a port that enables the controller 210 to connect or couple to a scan tool so that fault codes and other information regarding the vehicle may be obtained.

As also shown, the vehicle 202 includes the controller 300 and a telematics device 345. The controller 300 may be structured as one or more vehicle controllers/control systems, such as one or more electronic control units (ECU). The controller 300 may be separate from or included with at least one of a transmission control unit, an exhaust aftertreatment control unit, a powertrain control module, an engine control module or unit, or other vehicle controllers. In one embodiment, the components of the controller 300 are combined into a single unit. In another embodiment, one or more of the components may be geographically dispersed throughout the system or vehicle. In this regard, various components of the controller 300 may be dispersed in separate physical locations of the vehicle 202.

In one embodiment, the telematics device 345 may couple the vehicle 202 to the remote computing system 110 (and/or third party computing system 190) via the network 105. The telematics unit or device 345 may include, but is not limited to, a location positioning system (e.g., global positioning system) to track the location of the vehicle (e.g., latitude and longitude data, elevation data, etc.), one or more memory devices for storing the tracked data, one or more electronic processing units for processing the tracked data, and a communications interface for facilitating the exchange of data between the telematics device 345 and one or more remote devices (e.g., a provider/manufacturer of the telematics device 345, etc.). In this regard, the communications interface may be configured as any type of mobile communications interface or protocol including, but not limited to, Wi-Fi, WiMAX, Internet, Radio, Bluetooth, ZigBee, satellite, radio, Cellular, GSM, GPRS, LTE, and the like. The telematics device 345 may also include a communications interface for communicating with the controller 300 of the vehicle 202. The communication interface for communicating with the controller 210 may include any type and number of wired and wireless protocols (e.g., any standard under IEEE 802, etc.). For example, a wired connection may include a serial cable, a fiber optic cable, an SAE J1939 bus, a CAT5 cable, or any other form of wired connection. In comparison, a wireless connection may include the Internet, Wi-Fi, Bluetooth, ZigBee, cellular, radio, etc. In one embodiment, a controller area network (CAN) bus including any number of wired and wireless connections provides the exchange of signals, information, and/or data between the controller 300 and the telematics device 345. In still another embodiment, the communication between the telematics device 345 and the controller is via the unified diagnostic services (UDS) protocol.

In yet another embodiment, the controller 300 may be configured to communicate with the remote computing system 110 (and/or third party computing system 190) via the network 105 directly and without the usage of the telematics device 345. As shown, the controller 300 includes a communication interface 350. As alluded to above, the controller 300 may be structured to include the entirety of the communication interface 350 or include only a portion of the communications interface 350. In these latter embodiments, the communication interface 350 is communicatively coupled to the processing circuit 312 and the ODI modeling circuit 340. In other embodiments, the controller 300 is substantially separate from the communication interface 350. For example, the controller 300 and the communication interface 350 are separate control systems, but may be communicatively and/or operatively coupled. The communications interface 350 may include any combination of wired and/or wireless interfaces (e.g., jacks, antennas, transmitters, receivers, transceivers, wire terminals) for conducting data communications with various systems, devices, or networks structured to enable in-vehicle communications (e.g., between and among the components of the vehicle) and (in some embodiments, such as if a telematics device 345, such as telematics device 345, is not included or, in place of a telematics device 345) out-of-vehicle communications (e.g., directly with remote computing system 110). In this regard, in some embodiments, the communications interface 350 includes a network interface. The network interface is used to establish connections with other computing devices by way of the network 105. The network interface includes program logic that facilitates connection of the controller 300 to the network 105. The network interface includes any combination of a wireless network transceiver (e.g., a cellular modem, a Bluetooth transceiver, a Wi-Fi transceiver) and/or a wired network transceiver (e.g., an Ethernet transceiver). Thus, in some arrangements, the network interface includes the hardware and machine-readable media sufficient to support communication over multiple channels of data communication. Further, in some arrangements, the network interface includes cryptography capabilities to establish a secure or relatively secure communication session in which data communicated over the session is encrypted. For example and regarding out-of-vehicle/system communications, the communications interface 350 may include an Ethernet card and port for sending and receiving data via an Ethernet-based communications network and/or a Wi-Fi transceiver for communicating via a wireless communications network. The communications interface 350 may be structured to communicate via local area networks and/or wide area networks (e.g., the Internet) and may use a variety of communications protocols (e.g., IP, LON, Bluetooth, ZigBee, radio, cellular, near field communication). Furthermore, the communications interface 350 may work together or in tandem with a telematics device 345 in order to communicate with other vehicles in the fleet of one or more vehicles. In one example embodiment, the communications interface 350 is structured provide vehicle operational parameters and data to the remote computing system 110, the third party computing systems 190, and/or other vehicles in the fleet 200.

The controller 300 is shown to further include a processing circuit 312 and an oil drain interval (ODI) modeling circuit 340. In one embodiment, the ODI modeling circuit 340 is embodied as machine or computer-readable media storing instructions that are executable by a processor, such as processor 314. As described herein and amongst other uses, the machine-readable media facilitates performance of certain operations to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). The computer readable media may include code, which may be written in any programming language including, but not limited to, Java or the like and any conventional procedural programming languages, such as the "C" programming language or similar programming languages. The computer readable program code may be executed on one processor or multiple processors. In the latter scenario, the remote processors may be connected to each other through any type of network (e.g., CAN bus, etc.).

In another embodiment, the ODI modeling circuit 340 is embodied as a hardware unit, such as an electronic control unit. As such, the ODI modeling circuit 340 may be embodied as one or more circuitry components including, but not limited to, processing circuitry, network interfaces, peripheral devices, input devices, output devices, sensors, etc. In some embodiments, the ODI modeling circuit 340 may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the ODI modeling circuit 340 may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on). The ODI modeling circuit 340 may also include programmable hardware devices such as field programmable gate arrays, programmable array logic, programmable logic devices or the like. The ODI modeling circuit 340 may include one or more memory devices for storing instructions that are executable by the processor(s) of the ODI modeling circuit 340. The one or more memory devices and processor(s) may have the same definition as provided below with respect to the memory device 316 and processor 314. In some hardware unit configurations and as described above, the ODI modeling circuit 340 may be geographically dispersed throughout separate locations in the vehicle relative to other aspects of the controller 300. Alternatively and as shown, the ODI modeling circuit 340 may be embodied in or within a single unit/housing, which is shown as the controller 300.

In the example shown, the controller 300 includes a processing circuit 312 having a processor 314 and a memory device 316. The processing circuit 312 may be configured to execute or implant the instructions, commands, and/or control processes described herein with respect to the ODI modeling circuit 340. The depicted configuration represents the ODI modeling circuit 340 as machine or computer-readable media storing instructions thereon.

The processor 314 may be implemented as one or more processors, one or more application specific integrated circuits (ASIC), one or more field programmable gate arrays (FPGAs), a digital signal processor (DSP), a group of processing components, or other suitable electronic processing components. The one or more processors may be shared by multiple circuits. Alternatively or additionally, the one or more processors may be configured to perform or otherwise execute certain operations independent of one or more co-processors. In other example embodiments, two or more processors may be coupled via a bus to enable independent, parallel, pipelined, or multi-threaded instruction execution. All such variations are intended to fall within the scope of the present disclosure. The memory device 316 (e.g., RAM, ROM, Flash Memory, hard disk storage, etc.) may store data and/or computer code for facilitating the various processes described herein. The memory device 316 may be communicably coupled to the processor 314 to provide computer code or instructions to the processor 314 for executing at least some of the processes described herein. Moreover, the memory device 316 may be or include tangible, non-transient volatile memory or non-volatile memory. Accordingly, the memory device 316 may include database components, object code components, script components, or any other type of information structure for supporting the various activities and information structures described herein.

In some embodiments, the controller 300 is configured as an on-board computing device (e.g., onboard the vehicle) that determines the ODI for the vehicle directly. In these embodiments, the controller 300 includes an ODI modeling circuit 340. The ODI modeling circuit 340 is substantially similar to the ODI modeling circuit 140 of FIG. 1. For example, the ODI modeling circuit 340 is structured to generate a predicted ODI based on an oxidation rate determined based on vehicle operational parameters and an oxidation limit based on vehicle metadata. In arrangement, the ODI modeling circuit 340 is communicatively coupled to the processing circuit 312. The vehicle operational parameters and the vehicle metadata may be stored in the memory 316. In some embodiments, the at least a portion of the high resolution dataset 132 is stored in the memory 316 (or, in some embodiments of the ODI modeling circuit 340, in a memory of the ODI modeling circuit 340). In another embodiment, the ODI determination is performed by the remote computing system 110. In which case, the ODI modeling circuit 340 may be excluded from the controller 300. In some embodiments, a specific API may be provided to the controller 300 to enable acquisition of specific vehicle operational data (namely, a fuel economy of the vehicle, an idle time for the vehicle, and a PTO time for the vehicle in conjunction with metadata for the vehicle). The API then enables transmission of this data, via the communication interface (or the telematics device 345), to the remote computing system 110 that determines the ODI for the vehicle. In yet another embodiment, the functionality of the ODI modeling circuit 340 and 140 may be split between the remote computing system 110 and the controller 300. All such variations are intended to fall within the scope of the disclosure with examples of each described below.

Figure 3:
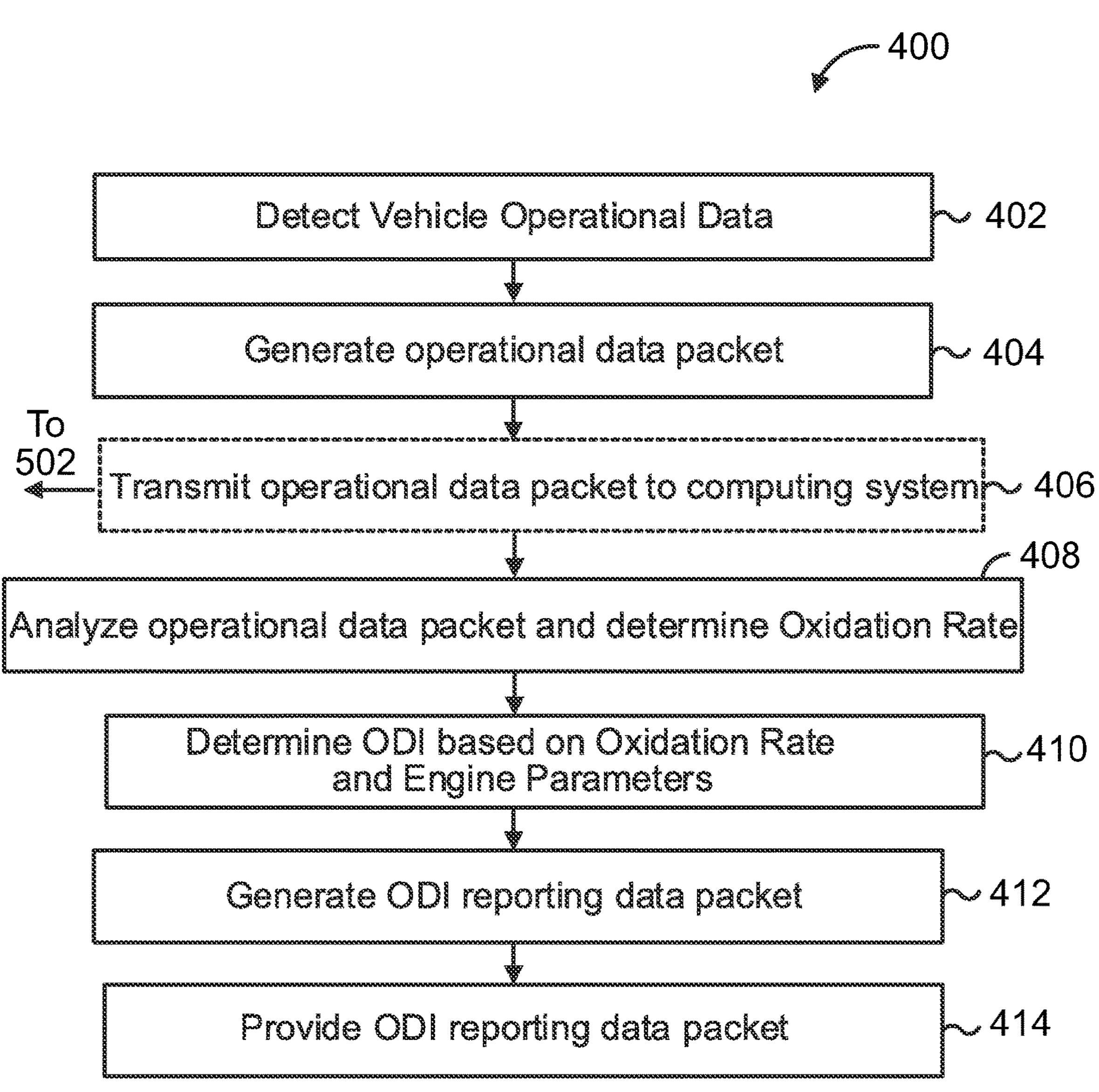
FIG. 3 is a flow diagram of a method of determining an oil drain interval, according to an example embodiment.

Referring now to FIG. 3, a flow diagram of a method of determining an oil drain interval of the vehicle 202 of FIGS. 1-2 is shown, according to an example embodiment. In some embodiments, one or more of the computing systems of the system 100 is configured to perform method 400. For example, the remote computing system 110, the third party computing system 190, and/or the controller 300, may be structured to perform the method 400. In the depicted example embodiment, the controller 300 performs the method 400, alone or in combination with other devices such as the remote computing system 110 and the third party computing systems 190. The method 400 may include user inputs from a user (e.g., a provider employee, a third-party employee, a customer, a vehicle operator, etc.) via one or more user devices (such as devices of provider employees, customer, a user device integrated with a vehicle, etc.).

As an overview of method 400, at process 402, vehicle operational data is detected. At process 404, an operational data packet is generated based on the detected or received operational data. At process 406, in a cloud computing embodiment, the operational data packet is transmitted to the remote computing system 110. After process 406, in the cloud computing embodiment, the method continues at process 502 of FIG. 4. In the on-board computing embodiment (i.e., local computing embodiment) as shown, process 406 may be omitted. At process 408, the operational data packet(s) are analyzed and an oxidation rate is determined by the controller 300. At process 410, an ODI is determined based on the oxidation rate and one or more engine parameters. At process 412, an ODI reporting data packet is generated. At process 414, the ODI data packet is provided. In some arrangements, the processes of the method 400 may be performed in a different order than as shown in FIG. 3 and/or the method 400 may include more or fewer steps than as shown in FIG. 3.

Referring to the method 400 in more detail, at process 402, vehicle operational data is detected. As described above, the vehicle 202 may include a sensor array that includes one or more sensors that detect or otherwise acquire data indicative of operation of various components or systems of the vehicle 202. The sensors may provide the detected operational data to the controller 300. In a virtual sensor embodiment, the controller 300 may determine certain operational data based on acquired other data (e.g., act as a virtual sensor; for example, the controller 300 may determine a vehicle speed based on a detected engine speed using one or more processes, algorithms, etc.). The operational data may include, but is not limited, information regarding a fuel economy of the vehicle, a total hours of operation of the engine, a value indicative of an idle time for the engine 355 for the vehicle (e.g., a percent of the total hours of operation), a value indicative of a PTO active time (e.g., a percent of the total of hours of operation), values regarding experienced engine load (e.g., an average engine load over a predefined time period, etc.), duty cycle parameters, and so on. In one embodiment, the fuel economy, idle time, and PTO time values for an entire life of the vehicle and engine. In another embodiment, the fuel economy, idle time, and PTO time values are for the vehicle since the last oil change. In yet another embodiment, the fuel economy, idle time, and PTO time values are determined for a different time frame (or, per-unit-of distance frame).

At process 404, an operational data packet is generated. The controller 300 generates an operational data packet including at least the vehicle operational data. The operational data packet may also include historical data and/or trend data such as sensor data over time, sensor data per a unit of distance (e.g., one mile), sensor data for a route or portion of a route, etc. In this regard, the operational data packet includes at least information regarding a fuel economy of the vehicle, a total hours of operation of the engine, a value indicative of an idle time for the engine 355 for the vehicle (e.g., a percent of the total hours of operation), and a value indicative of a PTO active time (e.g., a percent of the total of hours of operation). The operational data packet may also include metadata associated with the vehicle 202 and/or an engine (or another vehicle system or component) of the vehicle 202. The metadata may include identifying characteristics, such as an engine serial number (ESN), a vehicle identified number (VIN), an IP address for the controller 300 (or telematics device 345), a destination IP address (e.g., specific to the remote computing system 110), lubrication system model number, and any other identifier to enable it to be processed efficiently (e.g., categorized). The metadata may be in form of a value (e.g., numeric, alpha, alphanumeric) that is a tag to the data packet that informs of specifics of the source of the data. Thus, the metadata may enable a remote operator to drill down on the source of the data (e.g., an attendant of the remote computing system 110 or third party computing system 190). In this embodiment, by limiting the packet to this operational data and metadata, the operational data packet is relatively small in size and capable of being transmitted with low or intermitted network connectivity. In some embodiments, the operational data packet also includes other information, such as an indication of lube-oil status (e.g., a time since last changed, a number of lubrication changes over a predefined period such as since a build-date of the engine, etc.). Accordingly, in these embodiments, the operational data packet may include time data, location data, route information, operator information, and/or any of the information described herein.

At process 406, the operational data packet is transmitted to a computing system. As briefly described above, in a cloud computing embodiment, the operational data packet is transmitted to the remote computing system 110, and in a local computing embodiment, the operational data packet is provided to the ODI modeling circuit 340 of the controller 300. In this latter embodiment, there may be no "transmission" as the data may be accumulated and analyzed directly by the controller 300. This embodiment may be beneficial due to there being less reliance on network connectivity. In the former embodiment, the controller 300 is structured to transmit the operation data packet via the communications interface 350 (or, in some embodiments, via the telematics device 345) to the remote computing system 110.

At process 408, the ODI modeling circuit 340 analyzes the operational data packet and determines an oxidation rate. The "oxidation" amount, rate, etc. refers to the degradation of the oil. As described above, the ODI modeling circuit 340 generates one or more statistical models using the operational data packet including the one or more vehicle parameters, data stored in the memory 316 (or, in some embodiments of the ODI modeling circuit 340, in the ODI modeling circuit 340 itself), and/or data received from the remote computing system 110. The ODI modeling circuit 340 generates a regression equation based on the statistical model. The regression equation may be generated based on a best fit equation using one or more operational parameters such as a fuel efficiency, a fuel consumption rate, an idle and PTO time percentage, and the like. In generating the regression equation, the ODI modeling circuit 340 calculates the values of the constants $a_j$. The regression equation is used to determine an oxidation rate. Equation (1), shown above and reproduced below, provides an example process for determining the oxidation rate which as shown is a function of one or more variables $x_i$.

$$\text{Oxidation Rate} = da_0 + a_1(x_0) + a_2(x_0)^2 + a_3(x_1) + a_4(x_1)^2 + a_5(x_2) + a_6(x_2)^2 + \ldots + a_j(x_i) + a_{j+1}(x_i)^2 \quad (1)$$

In Equation (1), $a_j$ and d are constants. As mentioned above, the inputs of vehicle operational parameters ($x_i$), such as fuel economy, idle time, PTO time, and consequently idle and PTO time, may be determined by the controller 210 based on operating information regarding the engine 355 and vehicle. For example, the controller 300 may include a timer that starts/stops when the engine is turned on/off respectively, an idle sub-timer that starts when the engine is in an idle condition (e.g., engine on but vehicle not moving) and turns off when the idle condition is exited, and a PTO sub-timer that starts when the engine is used for a specific predefined function (e.g., with a crane, a drum from a concrete mixer truck, etc.) and stops when that function is ended. Based on this information, the controller 300 may determine a value indicative of an idle and PTO time and, particularly, a percentage that the engine 355 is in operating in an idle and PTO relative to a total time on for the engine.

According to one embodiment, the constant d is greater than one and, in particular, between one and six. The constant d, or adjustment value, is configured to limit instances of ODI over-prediction (i.e., causing too frequent ODIs that are unnecessary). In this regard, by using only fuel economy and idle and PTO time as inputs to the Oxidation Rate equation, the controller 300 is determining that there are no other sources of oxidation rate variation, which is likely not true as variation can occur from a variety of sources such as oil sump fill volume, part-to-part variation (e.g., liners), oil grade (standard, premium, etc.), etc. However, by using these three variables, a relatively faster ODI determination process may be achieved which technically reduces bandwidth requirements (when the ODI determination is performed by the remote computing system 110 because less data is transmitted over the network), technically leads to faster determinations due to utilizing relatively less data values, and may lead to determinations being able to be performed by the remote computing system 110 when they may otherwise not be capable of being performed because a sustained network connection may be required whereas only using these data points reduces the network connectivity time. Moreover, Applicant has determined that a relatively accurate ODI prediction is achieved with these few data points.

In another embodiment, the oxidation rate may be determined using Equation (3), shown below.

$$\text{Oxidation Rate} = E*\left(F - G(\text{fuel economy}) - H(\text{idle} + PTO\ \text{time}) + I(\text{idle} + PTO\ \text{time})^2\right) \quad (3)$$

In Equation (3), E, F, G, H, and I are constants. Relative to Equation (1), a factor (or multiplier), E, has been introduced to amplify or otherwise increase the oxidation rate. This multiplier hedges/protects against error in the oxidation rate using Equation (1) that only uses a few data points. By increasing the oxidation rate value, the determined ODI value decreases. In other words, the predicted or determined ODI value decreases (i.e., shortens the ODI). That said and notwithstanding, including the multiplier may result in relatively longer ODI's being achieved compared to service literature limits. It should be understood and as described herein that in other embodiments, different parameters, more parameters, or less parameters are used relative to those shown in Equation (3).

At process 410, the ODI modeling circuit 340 determines an ODI based on the oxidation rate determined at process 408 and one more engine parameters. The one or more engine parameters are determined based on engine or vehicle metadata. The one or more engine parameters include, for example, an oxidation limit based on an engine type, a lubricant oil type, and so on. In particular, the ODI modeling circuit 340 determines the ODI using Equation (2) shown above, and reproduced below, where "Abs" refers to absorbance and "cm" refers to centimeter (i.e., absorbance per centimeter which indicates the amount of contaminants, degradation and contaminants in the oil per centimeter).

$$\text{Oil Drain Interval} = \frac{\text{Oxidation Limit}\left(\frac{\text{Abs}}{\text{Cm}}\right)}{\text{Oxidation Rate}\left(\frac{\frac{\text{Abs}}{\text{cm}}}{\text{mile}}\right)} \quad (2)$$

Relative to that shown above, Equation (2) is shown to include units to show the conversion to ODI per unit distance (in this case, miles). In one embodiment, the oxidation limit is a predefined static value specific to a vehicle 202 system or component and, particularly, the engine 355 included in the vehicle 202. As an example, a 15 L type engine may have a predefined oxidation limit of 30,000 miles while a 6.7 L type engine may have a predefined oxidation limit of 20,000 miles. As another example, the predefined limit may be specific to the lubricant type, lubrication system, and/or other characteristic. In another embodiment, the oxidation limit is a predefined value that dynamically changes (e.g., with time and/or distance). For example, an initial oxidation limit for the 15 L may be 30,000 miles yet after 5 years or 100,000 miles, whichever occurs sooner, the predefined limit changes to 25,000 miles and after 125,000 miles or 7 years, whichever occurs sooner, the predefined limit changes to 20,000 miles. This embodiment may account for degradation of the system as a whole over time. The static and/or dynamic predefined oxidation limits may be stored in the ODI modeling circuit 340 for quick and easy retrieval (or, ODI modeling circuit 140 when utilized).

At process 412, an ODI reporting data packet is generated. The controller 300 generates an ODI reporting data packet including the oxidation rate and/or the determined ODI from process 410. At process 414, the ODI reporting data packet is provided to at least one of the remote computing system 110 or the third party computing systems 190 by the controller 300 directly (e.g., via the communications interface 350) or via the telematics device 345.

In one embodiment, the controller 300 may compare the determined ODI to a predetermined ODI. The predetermined ODI may be stored by the controller 300 and be specific to at least one of the engine type, lubricant type, etc. Based on the comparison indicating that a ODI is needed or needed within a predefined amount of distance (e.g., less one-hundred miles) or estimated time (e.g., less than two weeks) (i.e., the determined ODI exceeds the predefined ODI), the controller 300 may implement a variety of actions. For example and in response to the determination that the ODI is needed and has been needed by more than a predefined amount of time or another metric (e.g., miles over the predefined ODI), the controller 300 may communicate with the remote computing system 110 to retrieve a map (or retrieve a map stored in memory), surface the map through the I/O device 365, and identify nearby service stations on the map for the vehicle 202 to address the ODI. In combination, the controller 300 may cause haptic feedback, such as a vibrating of the operator's seat of the vehicle 202 to indicate that service is needed. In another embodiment, the controller 300 may trigger an indicator (e.g., one or more fault codes with a malfunction indicator lamp, etc.) based on the comparison (for example, if the comparison indicates that the ODI exceeds the predetermined ODI but not by the predefined amount). The controller 300 may also provide an indication that the determined ODI does not require service based on the comparison by, for example, providing a graphical depiction via the I/O device 365 (a textual message, such as "No Action Required.") (e.g., if the determined ODI does not exceed the predetermined ODI).

Figure 4:
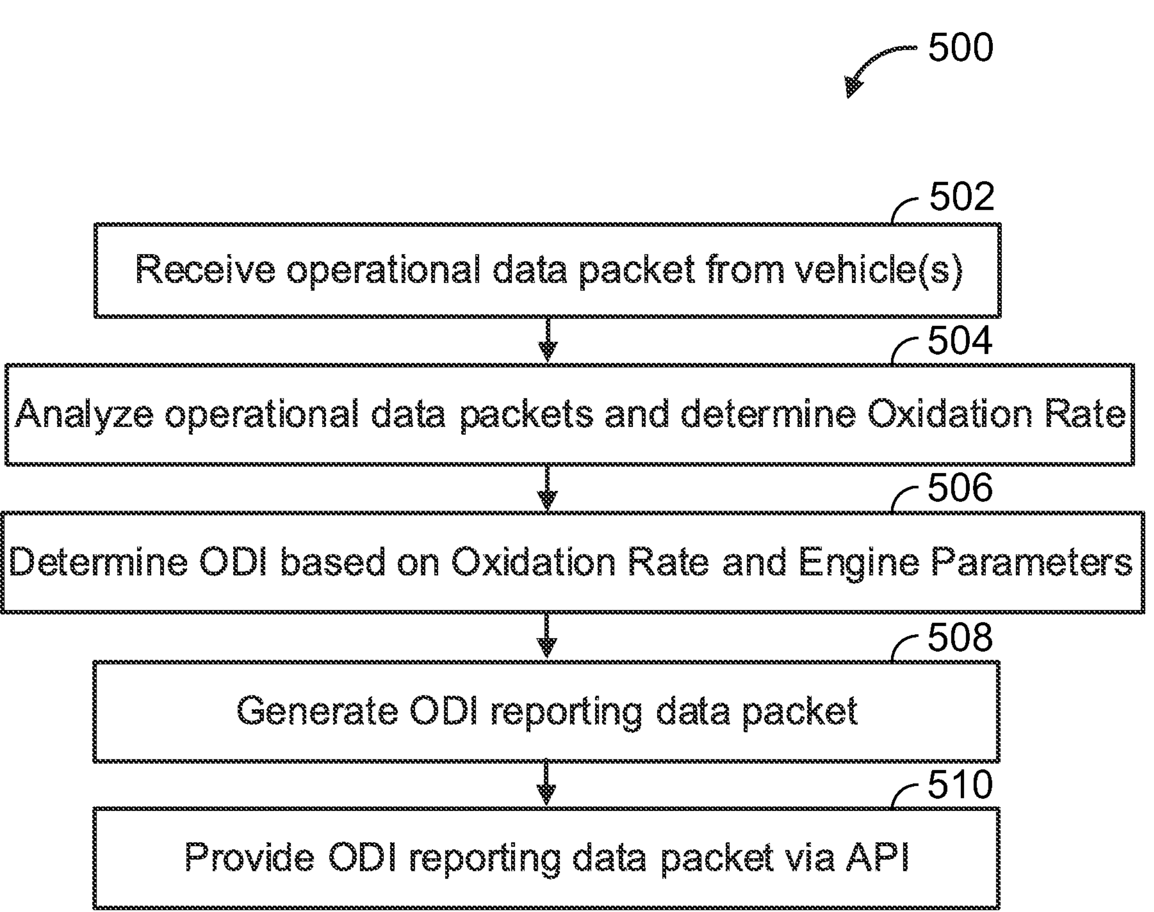
FIG. 4 is a flow diagram of a method of determining an oil drain interval by a computing system of FIG. 1, according to an example embodiment.

FIG. 4 is a flow diagram of a method 500 of determining an oil drain interval by a computing system of FIG. 1, according to an example embodiment. In some embodiments, one or more of the computing systems of the system 100 is configured to perform method 500. For example, the remote computing system 110, the third party computing system 190, and/or the controller 300, may be structured to perform the method 500. In an example embodiment, the remote computing system 110 performs the method 500, alone or in combination with other devices such as the controller 300 and the third party computing systems 190. The method 500 may include user inputs from a user (e.g., a provider employee, a third-party employee, a customer, a vehicle operator, etc.) one or more user devices (such as devices of provider employees, customer, a user device integrated with a vehicle, etc.), another computing device on the network 105, etc.

As an overview of method 500, at process 502, an operational data packet is received from one or more vehicles 202. At process 504, the operational data packets are analyzed and an oxidation rate is determined. At process 506, an ODI is determined based on oxidation rates and engine parameters. At process 508, an ODI reporting data packet is generated. At process 510, the ODI data packet is provided via an application programming interface. In some arrangements, the steps of the method 500 may be performed in a different order than as shown in FIG. 4 and/or the method 500 may include more or fewer steps than as shown in FIG. 4. For example, process 510 may not be included in the method 500.

Referring to the method 500 in more detail, at process 502, an operational data packet is received by the remote computing system 110 from one or more vehicles 202. The operational data packet includes vehicle operational data and vehicle metadata as described above.

At process 504, the operational data packets are analyzed and an oxidation rate is determined. As described above, the ODI modeling circuit 140 generates one or more statistical models using the operational data packet including the one or more vehicle parameters, data stored in the database 130. The ODI modeling circuit 140 and generates a regression equation based on the statistical model. The regression equation may be generated based on a best fit equation using one or more operational parameters such as a fuel efficiency, a fuel consumption rate, an idle and PTO time percentage, and the like. The regression equation, shown herein as Equation (1) (and Equation (3) in some embodiments), is used to determine an oxidation rate.

At process 506, an ODI is determined based on oxidation rates and engine parameters. The ODI modeling circuit 140 determines an ODI based on the oxidation rate determined at process 504 and one more engine parameters. The one or more engine parameters are determined based on engine or vehicle metadata. The one or more engine parameters include, for example, an oxidation limit based on an engine type, a lubricant oil type, and so on.

At process 508, an ODI reporting data packet is generated. The remote computing system 110 generates an ODI reporting data packet including the oxidation rate and/or the ODI. At process 510, the ODI reporting data packet is provided to the third party computing systems 190 via the API hosted by the API circuit 146. For example, the ODI reporting data packet is transmitted to the third party computing systems via the API circuit 146 and communications interface 350.

In contrast to the method 400, in this embodiment, the remote computing system 110 may perform the comparison of the determined ODI relative to a predefined ODI stored by the remote computing system 110. In response, the remote computing system 110 may provide an instruction over the network to the controller 300 of the vehicle to, for example, derate the engine, trigger a fault code, illuminate an indicator (e.g., a malfunction indicator lamp/light), and/or another specific control process. Additionally, the remote computing system 110 may generate and provide a map of nearby service locations for the vehicle 202 based on a current location of the vehicle 202. In this regard, the remote computing system 110 may track location data of the vehicle 202 in order to identify nearby service locations (e.g., the vehicle operational data may include location data that is transmitted to the remote computing system 110).

The remote computing system 110 may also generate a graphical user interface for display on a computing device. In this regard, the remote computing system 110 may provide the determined ODI to an output computing device. The graphical user interface may depict fleet data including, but not limited to, determined ODIs for the vehicles in the fleet. The determined ODIs may be distributed on a map associated with a location of the corresponding vehicle. Upon selection of the determined ODI icon, a drill down menu may be provided showing vehicle data (e.g., engine serial number, software calibration information for the controller 300, etc.). The data points may be color coded so that fleet operators or other operators can quickly observe how the determined ODIs for each vehicle compare to predetermine ODIs for the vehicle. Thus, fleet operators may be able to quickly see which vehicles require servicing, where the vehicles are located, etc.

In some embodiments, the controller 300 may only transmit the operational data packet in certain times of operation. For example, the controller 300 may only transmit or cause transmission (e.g., via the telematics device 345) when the network connectivity is above a predefined threshold for a predefined amount of time (e.g., thirty minutes). In another example, the controller 300 may examine the location surrounding the vehicle 202 to determine whether to transmit the data packet or not (e.g., if the area is a metropolitan area, there is a high likelihood of sustained connectivity such that the data packet may be transmitted without network interruptions). In still other examples, the times of operation may include specific operating parameters of the vehicle. For example, the controller 300 may transmit the data packet when the vehicle 202 is in an idle condition so that potential issues with network connectivity when the vehicle 202 is moving are mostly alleviated.

Figure 5:
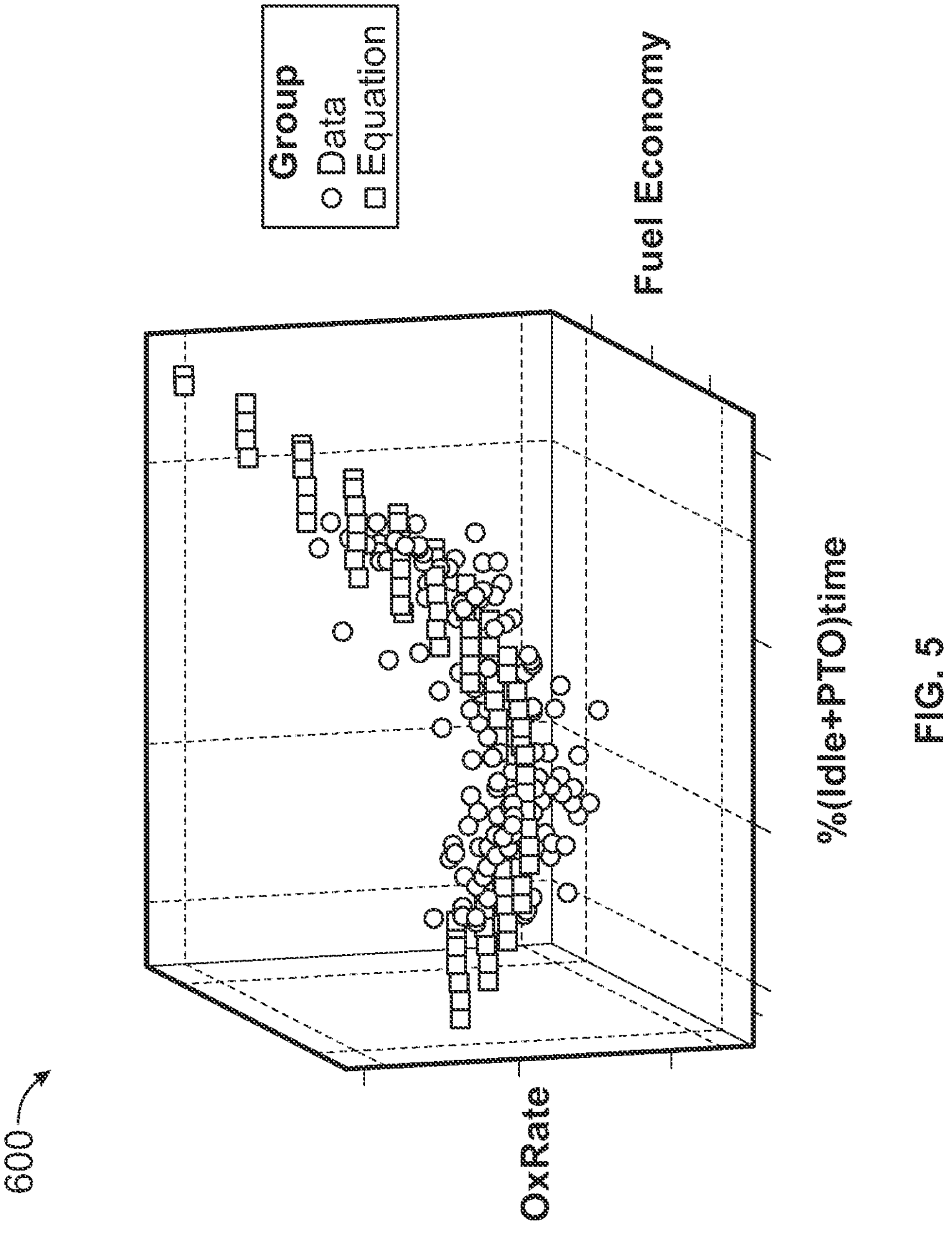
FIG. 5 is a three-dimensional scatter plot of an oxidation rate versus fuel economy versus a percentage idle and power take off time, according to an example embodiment.
Figure 6:
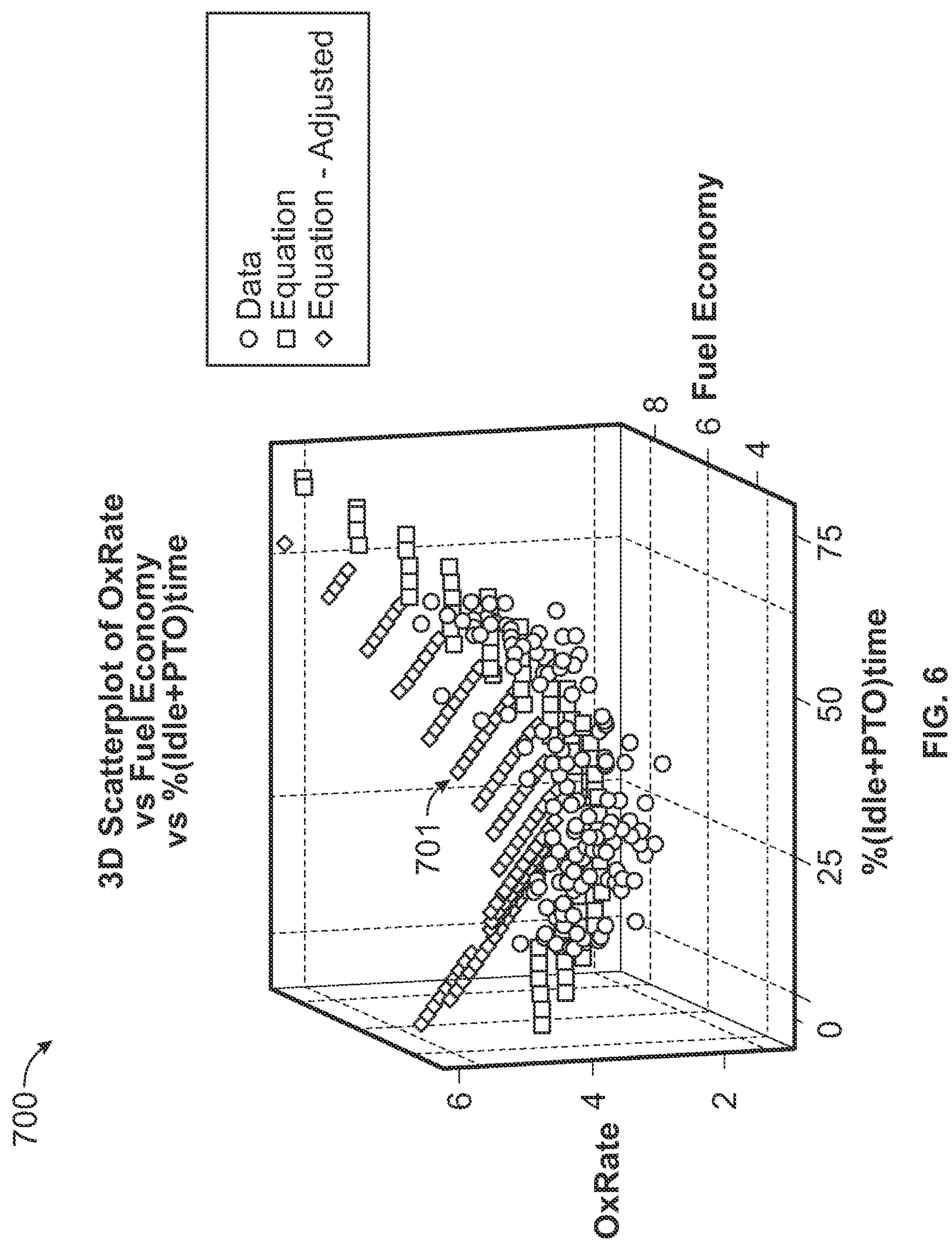
FIG. 6 is another three-dimensional scatter plot of an oxidation rate versus fuel economy versus a percentage idle and power take off time, according to an example embodiment.

FIG. 5 is a three-dimensional scatter plot 600 of an oxidation rate versus fuel economy versus a percentage idle and power take off time, according to an example embodiment. The rounded points depict vehicle operational data that is provided to the remote computing system 110. As discussed above, the vehicle operational data is provided in real-time or in near-real time such that the model is updated based on current information. The square points depict predicted or data generated by a regression equation and, particularly Equation (1), as described above. In comparison, FIG. 6 shows a plot 700 with the same/similar data but also using Equation (3) (701). Relative to the regression Equation (1), Equation (3) increases the oxidation rate to account for other variables not captured by Equation (1) (i.e., more than fuel economy, idle time, and PTO time). Some applications may desire the use of Equation (3) in order to decrease ODIs while other applications may desire Equation (1) to extend ODIs.

In other embodiments, the statistical models and/or regression equations may be generated based on other vehicle operational parameters including, but not limited to, the vehicle operational parameters described herein with respect to FIG. 1.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using one or more separate intervening members, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic. For example, circuit A communicably "coupled" to circuit B may signify that the circuit A communicates directly with circuit B (i.e., no intermediary) or communicates indirectly with circuit B (e.g., through one or more intermediaries).

While various circuits with particular functionality are shown in FIGS. 1 and 2, it should be understood that the remote computing system 110 and/or the controller 300 may include any number of circuits for completing the functions described herein. For example, the ODI modeling circuit 140 and/or the ODI modeling circuit 340 may be distributed into multiple circuits or combined as a single circuit. Additional circuits with additional functionality may also be included. Further, the controller 300 may further control other activity beyond the scope of the present disclosure.

As mentioned above and in one configuration, the "circuits" may be implemented in machine-readable medium storing instructions (e.g., embodied as executable code) for execution by various types of processors, such as the processor 314 of FIG. 2. Executable code may, for instance, comprise one or more physical or logical blocks of computer instructions, which may, for instance, be organized as an object, procedure, or function. Nevertheless, the executables need not be physically located together, but may comprise disparate instructions stored in different locations which, when joined logically together, comprise the circuit and achieve the stated purpose for the circuit. Indeed, a circuit of computer readable program code may be a single instruction, or many instructions, and may even be distributed over several different code segments, among different programs, and across several memory devices. Similarly, operational data may be identified and illustrated herein within circuits, and may be embodied in any suitable form and organized within any suitable type of data structure. The operational data may be collected as a single data set, or may be distributed over different locations including over different storage devices, and may exist, at least partially, merely as electronic signals on a system or network.

While the term "processor" is briefly defined above, the term "processor" and "processing circuit" are meant to be broadly interpreted. In this regard and as mentioned above, the "processor" may be implemented as one or more processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

Embodiments within the scope of the present disclosure include program products comprising computer or machine-readable media for carrying or having computer or machine-executable instructions or data structures stored thereon. Such machine-readable media can be any available media that can be accessed by a computer. The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing. More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device. Machine-executable instructions include, for example, instructions and data which cause a computer or processing machine to perform a certain function or group of functions.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present disclosure may be written in any combination of one or more other programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the apparatus and system as shown in the various exemplary embodiments is illustrative only. Additionally, any element disclosed in one embodiment may be incorporated or utilized with any other embodiment disclosed herein.

What is claimed is:

1. A computing system comprising:
- a communication interface structured to communicably couple to a network;
- one or more processors;
- a memory storing instructions that, when executed by the one or more processors, cause the one or more processors to:
  - receive, via the communication interface and from a vehicle, vehicle operational data and vehicle metadata;
  - receive an operational data packet comprising at least one of the vehicle operational data, trend data, or the vehicle metadata;
  - determine a lubricant oxidation rate based on the operational data packet and a statistical model;
  - determine a lubricant drain interval based on the lubricant oxidation rate;
  - generate a lubricant drain interval reporting data packet;
  - provide the lubricant drain interval reporting data packet to an output device;
  - compare the lubricant drain interval to a predefined lubricant drain interval; and
  - in response to the comparison, derate an engine of the vehicle by transmitting an instruction over the network via the communication interface.

2. The computing system of claim 1, wherein the lubricant oxidation rate is based on less than four operational data values.

3. The computing system of claim 1, wherein the lubricant oxidation rate is based on a fuel economy, an idle time of an engine of the vehicle, and a power take-off time of the vehicle.

4. The computing system of claim 1, wherein in response to the comparison, the one or more processors are further configured to cause an indicator on the vehicle to illuminate.

5. The computing system of claim 1, wherein in response to the comparison, the one or more processors are further configured to generate and provide a map to the vehicle with a direction to a service location, wherein the map is displayed by the vehicle.

6. The computing system of claim 1, wherein in response to the comparison, the one or more processors are further configured to trigger one or more fault codes for the vehicle.

7. The computing system of claim 1, wherein the instructions, when executed by the one or more processors, further cause the one or more processors to parse the vehicle metadata from the vehicle operational data and associate the vehicle metadata with a record associated with the vehicle.

8. The computing system of claim 1, wherein the lubricant is oil.

9. A method of determining a lubricant drain interval, the method comprising:
- receiving, by a computing system, vehicle operational data and vehicle metadata from a vehicle;
- receiving, by the computing system, an operational data packet comprising at least one of the vehicle operational data, trend data, or the vehicle metadata
- determining, by the computing system, a lubricant oxidation rate based on the operational data packet and a statistical model;
- determining, by the computing system, a lubricant drain interval based on the lubricant oxidation rate;
- generating, by the computing system, a lubricant drain interval reporting data packet;
- providing, by the computing system, the lubricant drain interval reporting data packet to an output device;
- comparing, by the computing system, the lubricant drain interval to a predefined lubricant drain interval; and
- derating, by the computing system, an engine of the vehicle by transmitting an instruction over the network responsive to determining that the lubricant drain interval exceeds the predefined lubricant drain interval.

10. The method of claim 9, wherein determining the lubricant oxidization rate is based on less than four operational data values.

11. The method of claim 9, further comprising:
- responsive to determining that the lubricant drain interval exceeds the predefined lubricant drain interval, causing, by the computing system, an indicator on the vehicle to illuminate.

12. The method of claim 9, further comprising:
- responsive to determining that the lubricant drain interval exceeds the predefined lubricant drain interval, generating, by the computing system, a map comprising a direction to a service location; and
- providing, by the computing system, the map to the vehicle, wherein the map is displayable by the vehicle.

13. The method of claim 10, further comprising responsive to determining that the lubricant drain interval exceeds the predefined lubricant drain interval, triggering, by the computing system, one or more fault codes for the vehicle.

14. The method of claim 9, further comprising modifying, by the computing system, the lubricant drain interval by a predetermined factor such that a modified lubricant drain interval is greater than the lubricant drain interval.

15. A system, comprising:

a controller coupled to an engine and at least one sensor of a vehicle, the controller compromising:

one or more processors; and at least one memory coupled to the one or more processors, the at least one memory storing instructions therein that, when executed by the one or more processors, cause the one or more processors to:

receive vehicle operational data from the at least one sensor;

generate an operational data packet comprising at least one of the vehicle operational data, trend data, or metadata;

determine an oxidation rate based on the operational data packet and a statistical model;

determine a lubricant drain interval based on the oxidation rate;

generate a lubricant drain interval reporting data packet;

provide the lubricant drain interval reporting data packet to an output device;

compare the lubricant drain interval to a predefined lubricant drain interval; and derate an engine of the vehicle responsive to determining that the lubricant drain interval exceeds the predefined lubricant drain interval.

16. The system of claim 15, wherein the instructions, when executed by the one or more processors, further cause the one or more processors to transmit the operational data packet to the output device prior to determining the oxidation rate.

17. The system of claim 15, wherein the oxidation rate is further based on one or more engine parameters, the one or more engine parameters comprising at least one of a fuel economy, an idle time, or a power take off time of the engine; and wherein the lubricant oxidation rate is based on less than four operational data values.

18. The system of claim 15, wherein the instructions, when executed by the one or more processors, further cause the one or more processors to receive at least one of (i) one or more data sets or (ii) one or more regression equations from the output device;

wherein determining the lubricant drain interval is further based on the at least one of (i) the one or more data sets or (ii) the one or more regression equations.

* * * * *